(12) United States Patent
Chang

(10) Patent No.: US 8,092,669 B2
(45) Date of Patent: Jan. 10, 2012

(54) SYSTEM AND METHOD OF EXAMINING TRACE ORGANIC MATTERS IN LIVING BEING'S URINE

(75) Inventor: An-Chih Chang, Hsinchu (TW)

(73) Assignee: Blincofa Biomedical Technology Corp., Hsinchu (TW)

( * ) Notice: Subject to any disclaimer, the term of this patent is extended or adjusted under 35 U.S.C. 154(b) by 960 days.

(21) Appl. No.: 11/988,097

(22) PCT Filed: Jul. 14, 2005

(86) PCT No.: PCT/CN2005/001044
§ 371 (c)(1),
(2), (4) Date: Dec. 31, 2007

(87) PCT Pub. No.: WO2007/006180
PCT Pub. Date: Jan. 18, 2007

(65) Prior Publication Data
US 2009/0152131 A1 Jun. 18, 2009

(51) Int. Cl.
*G01N 27/327* (2006.01)
*G01N 27/333* (2006.01)
(52) U.S. Cl. .... 205/792; 205/775; 205/787; 204/403.01
(58) Field of Classification Search ............. 204/403.01–403.15, 416–418; 205/775, 789, 777.5, 789.5, 792
See application file for complete search history.

(56) References Cited

U.S. PATENT DOCUMENTS 3,922,205 A * 11/1975 McLean et al. ............... 205/782
RE29,703 E * 7/1978 Fatt .............................. 600/356

FOREIGN PATENT DOCUMENTS

GB 2216267 A * 10/1989
SU 312620 A * 7/1969

OTHER PUBLICATIONS

Omanović et al. "Automation of Voltammetric Measurements by Polarographic Analyser PAR 384B," Croatia Chemica Acta CCACCAA 71(2) 421-433 (1988).*
Mirčeski et al. "Processing of the Data obtained from the Polarographic Analyzer Princeton Applied Research Model 384B by the Programming Package QPRO," Bulletin of the Chemists and Technologists of Macedonia, vol. 14, No. 1, p. 61-64 (1995).*
Derwent English langauge abstract for Soviet Union patent SU 312620 A, patent published on Jul. 7, 1969.*

* cited by examiner

*Primary Examiner* — Alex Noguerola
(74) *Attorney, Agent, or Firm* — Stites & Harbison PLLC; Juan Carlos A. Marquez, Esq.

(57) ABSTRACT

A method and a system of examining trace organic matter in urine are provided. The system includes a polarograph having a graphite electrode and a metal electrode; a data examining device having a memory device stored with a standard determination module, a comparison module and a display device for operating interface and displaying results. The examining method is to utilize a polarograph for examining living being's urine and store the polarogram produced by the polarograph in memory device. Then utilizing a comparison module to process comparison of the graph data of a polarogram with a standard determination module to examine the composition and quantity of an organic matter in urine, and displaying the result on a display device.

2 Claims, 3 Drawing Sheets

SYSTEM AND METHOD OF EXAMINING TRACE ORGANIC MATTERS IN LIVING BEING'S URINE

This application is a 371 of PCT/CN2005/001044, filed on Jul. 14, 2005.

BACKGROUND OF THE INVENTION

1. Field of Invention

This invention relates to a system that examines trace organic matter in a living being's urine, and in particular relates a polarographic technique that utilizes a solid-state electrode to measure the type and density of a trace organic matter in urine. The method proclaimed in this invention can provide physiological information of a living being so that it can be provided for further usage of examination and determination.

2. Related Art

Metabolic reactions of a living being, no matter it's having food and drink, falling ill, medicating, pathological changes of visceral organs . . . etc., all will be revealed by types of trace organic matters and changes of composition in a living being's urine. Taking human being as an example, no matter it's pregnant or not, drug abuse, steroids taking, AIDS infecting . . . etc., all have related urine examination techniques and products. Not only for human being but also for animals, in veterinarians or pasturage, all will apply urine examination techniques. Therefore, it's been well understood that trace organic matter examinations in urine is an important technique for diagnosing living being's physiological conditions.

On the development of urine examination techniques, the main difficulty is on how to detect some types of trace and specific organic matter from the examining matter of such composition complex urine. In all the examination techniques, the polarography in electrolytic analyses is a method, under special conditions, used to electrolyzing the solution of an examining matter and analyzing the procured electric voltage-current curve line. The theory base is to observe the electricity nature of an examining matter, and according to electricity dependence, to determine the property and quantity of an examining matter. A polarograph includes two electrodes: a reference electrode and an operation electrode. In examination, with the electrodes connected on, an examining matter is put into electrolyte, and the electrolyte is collected to base on for determination.

A polarography not only can examine elements of the periodic table, but also can analyze most of organic matters, such as: simple sugar, open but non-ring-type ketone or aldehyde, and some amino acids, such as: cysteine, histidine, aspartic acid, arginine, asparagines, methionine, etc. This method can process qualitative and quantitative analyses in the meantime and examine different matters at one experiment with high sensitivity and accuracy. Comparing with other methods, it has faster characteristic, gives more objective results with voluntary attainment of information, and can examine both trace solution and organic body fluid. And these examination results can provide ready information to the experimenter to determine the physiological states of an examining living being.

The structure of a conventional polarography, as FIG. 1 shows, comprises an electrolysis vessel 03 filled with the examining solution, wherein a mercury electrode 01 and a calomel electrode 02 dipped into, with which the calomel electrode 02 is a positive pole (a reference electrode) and the mercury electrode 01 is a negative pole (an operation electrode). The mercury electrode 01 is consisted of a mercury beaker 011 connected through a rubber pipe 012 with a capillary 013. By the adjustment of the height of the mercury beaker 011, it can adjust mercury drops' dropping speed, in general, every 10 seconds with 2 to 3 drops.

During electrolysis, adding a potential difference to the two electrodes and using a voltage meter 04 to indicate the numerical value and a current meter 05 to record the correspondent current value.

But mercury has a lot of shortcomings and is highly dangerous, it's very inapplicable, especially when using on clinical application. Mercury causes a great number of peracute and chronic diseases, so that a mercury operation place has to be quarantined and equipped with special facilities; otherwise, it will be dangerous. And mercury vapors in an unventilated working place will also cause a great problem. And it can't work, neither, in the industry, because the voltage surpasses 0.3 volts, it will cause the dissolution of positive ion of mercury. When the electrolysis speed increases, mercury flows out from a capillary. On an oscilloscope, which displays half-wave potential during the oscilloscope's process, a half-wave potential is displayed, and at the change of time axle, an electric pulse reaches to another mercury drop, but the spread of a mercury drop constantly does not let analyzing processed under the needed electric field and it can not be displayed either on the oscilloscope. The interval of mercury drops, under the same other conditions, is determined according to the amount of lost potential. Thus, when the secondary voltage increases to higher than the maximum of an electrical micro tube, the polarograph will cause a diffused electric current decrease. A fitting electric current always is a hindering factor, and mercury droppings cannot catch up with the electrode reaction. In other words, the test tempo is limited. In addition, at a high temperature, mercury will evaporate very fast that the vaporized mercury will bring away part of the examining matter, this will bring the problem of an inaccurate result for a trace matter examination.

Other than the problem caused by utilizing mercury electrodes, conventional polarographies still have other drawbacks, i.e., on the examination of the result, the examiner needs to read the number or the indicator hand that displayed on the screens of a current meter and a voltage meter. The drawbacks are: First, it lacks the accuracy. To observe from an indicator hand or a wave pattern of a current meter and a voltage meter is basically a naked eye method, as a smaller change of an indicator hand and a wave pattern will not be differentiated by an observer. Secondly, wave length observation accuracy is depending on the experience of an observer. So it will take longer time to train an operating staff. Thirdly, different observers might have different views of the same wave pattern that an examination result will not be objective.

As thus described above, we can understand in conventional techniques utilizing a polarograph with mercury for electrodes in a large number of clinical application has some problems. And further, a monitor that displaying an examination result, such as an oscilloscope, at the determination and examination of an examination result, still exits an inaccuracy and taking longer time for training an operation stuff problems that it still can not be named to be used in a great number on clinical application. Therefore, how to solve the problem of a mercury electrode and promote the ability of analyzing an examination result is a problem that we have to face and overcome.

SUMMARY OF THE INVENTION

One aspect of this invention is to provide a trace organic matter examination system in a urine examination. The system relates to a solid state electrode polarograph or a system that integrates a solid state electrode polarograph and a computer information technology, and in particular a system that integrates a solid state electrode polarography and a computer information technology to examine automatically the examination result through comparison of an obtained examination result with a standard determination data.

The other aspect of this invention is to provide a density examination system of the trace organic matter in a urine examination. The system comprises a polarography having at least one circuit connecting terminal, a graphite electrode connected with the circuit connecting terminal of the polarography through a conductive wire as an operation electrode, and a metal electrode connected with the circuit connecting terminal of the polarography through a conductive wire as a reference electrode. The system can be used for examining the densities of trace organic matters in urine, such as: simple sugar, open but non-ring-type ketone or aldehyde, and some amino acids.

An examination system of a solid state electrode polarograph relates to a polarograph utilizes a graphite electrode for operation electrodes which finished by a degassing and filling process. When utilizing the examination system, it needs to follow the following few steps:

1. Collecting a living being's urine as an examining matter, the living being can be a human being or a livestock;

2. Utilizing the solid state electrode polarograph to examine the urine to obtain a polarogram;

3. An examiner, according to his own knowledge and experience, from the electric voltage-current pattern of the polarogram obtains the type and density of a trace organic matter in an examining living being's urine;

4. From the density and type of a trace organic matter in urine to determine the physiological condition of the living being.

As a polarogram wave pattern is only an according to time change electric voltage-electric current signal, by utilizing electronic information technology, it can be completely read and recorded in a computer system. Therefore, the solid state electrode of a polarograph connects with a computer system, and through a communication interface such as RS232, USB . . . etc., a polarogram wave pattern value is delivered to the computer system and stored in the memory device. Then, utilizing a comparison module, the polarogram and a standard determination data are compared. The standard determination data is a digit or a graph that to be based on to determine the correlative physiological condition of a polarogram. Thus, the electronic information technology can be utilized to analyze automatically an examination result to assist or to replace the conventional determination method.

DETAILED DESCRIPTION OF THE PREFERRED EMBODIMENTS

Embodiment 1

A System of Examining Trace Organic Matter in Urine

Figure 1:
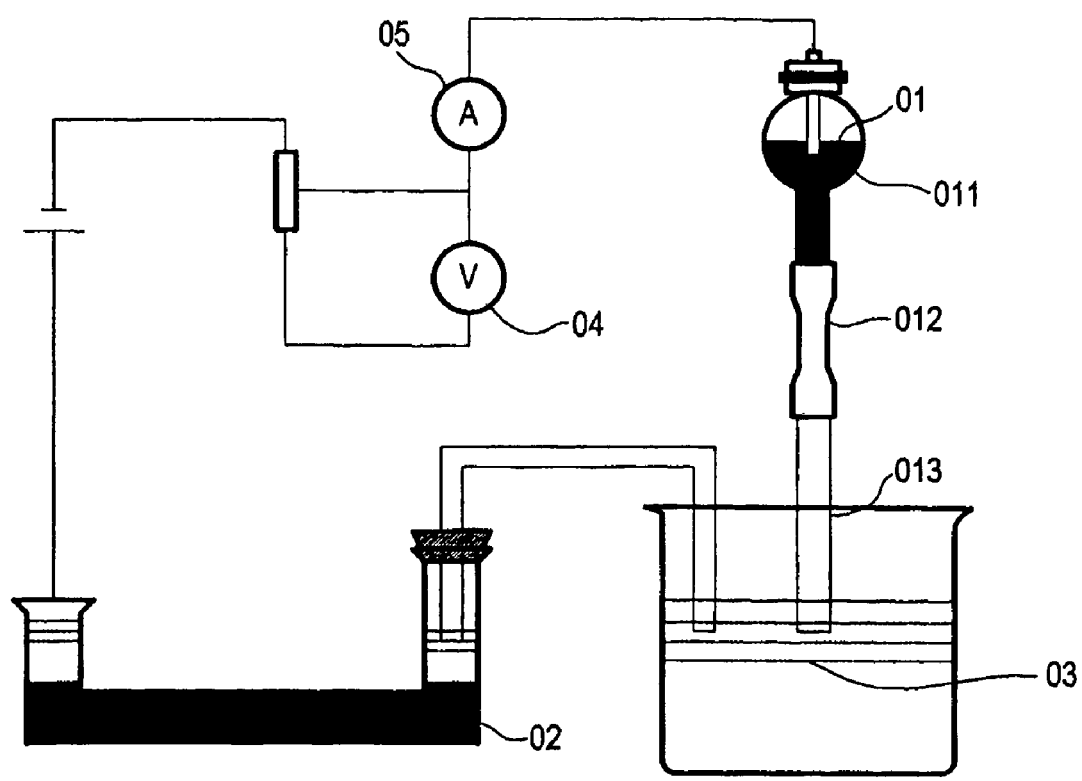
FIG. 1 is a conventional polarograph.
Figure 2:
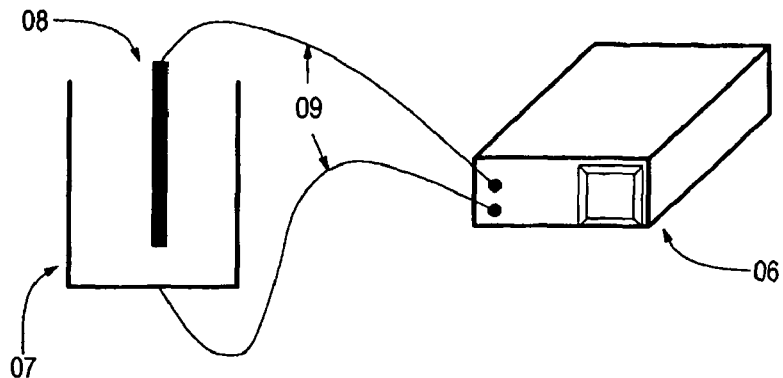
FIG. 2 is a schematic diagram of a system applied to examining trace organic matter in urine of this invention.

As FIG. 2 shows, it's a schematic diagram of a system of examining trace organic matter in urine, wherein includes a polarograph 06 (integrating a circuit and components of a polarograph's originated voltage meter, current meter . . . etc. into a shell of shown in FIG. 1), wherein a positive pole through a conductive wire connects with a metal electrode 07 (a reference electrode), and a polarograph's negative pole connects with a graphite electrode 08 (an operation electrode). The system can be used for examining the densities of trace organic matters in urine, such as: simple sugar, open but non-ring-type ketone or aldehyde, and some amino acids, such as: cysteine, histidine, aspartic acid, arginine, asparagines, methionine, etc. In addition, for easily obtaining reading, the polarograph 06 may further connect with outputting devices such as printers or display devices.

A production method for the graphite electrode 08 is a finish of degassing and filling process. The degassing and filling process comprises:

1. Degassing process: utilizing a vacuum system to degas the air molecules from a graphite electrode structure;

2. Filling process: filling stuff in vacant spaces of a graphite electrode.

The object of a degassing and filling process is to remove the air from vacant spaces of a graphite electrode structure to reduce the molecules that will interfere electrolysis reaction. Another object is to draw out these air molecules in vacant spaces of a graphite electrode to facilitate stuff filling in the vacant spaces so that the air will not refill into these vacant spaces.

Embodiment 2

A System of Automatically Examining Trace Organic Matter in Urine

Figure 3:
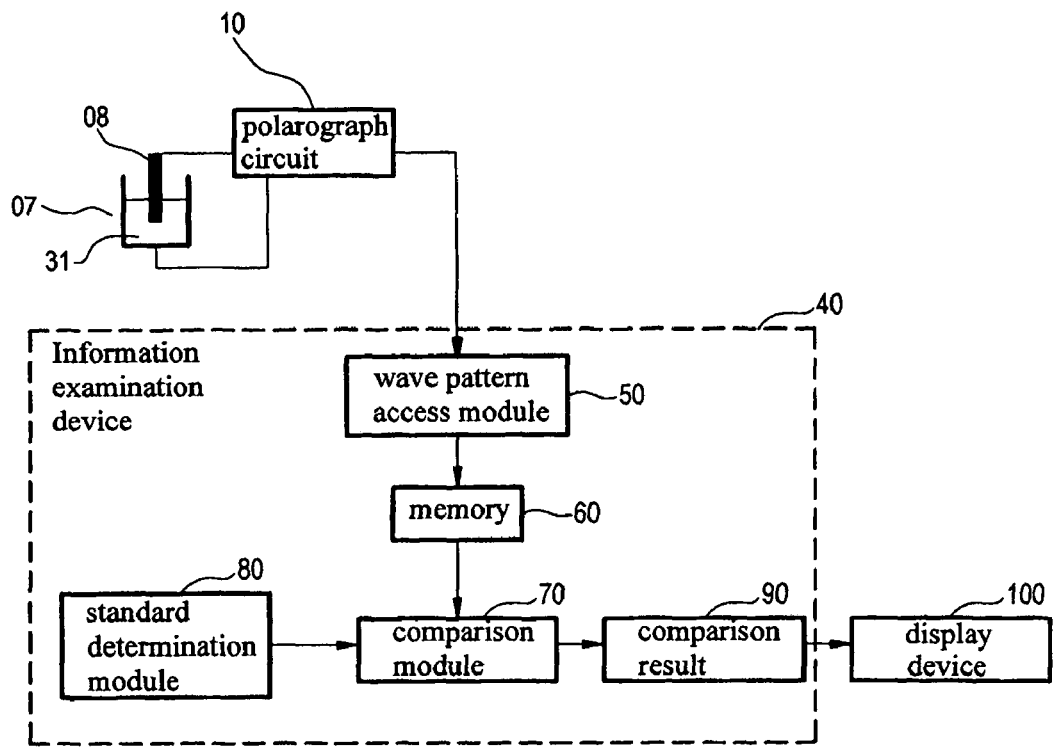
FIG. 3 is a circuit diagram view of a system applied to examining trace organic matter in urine of this invention.

As FIG. 3 shows, it's a system of automatically examining trace organic matter in urine, wherein a polarograph circuit 10 connects with a finished graphite electrode 08 (an operation electrode). The material of the graphite electrode 08 is a graphite, wherein it can be glassy graphite, graphite paste, spectrum graphite, etc. The external surface of the graphite electrode 08 is applied a layer of stuff. In this embodiment, the stuff is paraffin, wherein others of the same can be used also such as: wax, BF glue, rosin, etc.

The material of the metal electrode 07 (a reference electrode) in this embodiment is to use aluminum, wherein others of the same can be used also such as: gold, platinum, silver, titanium, molybdenum, vanadium, wolfram, hard aluminum, etc. The metal electrode 07 is formed with a beaker shape, which is put with examining matter 31 of urine. The graphite electrode 08 is dipped into the urine examining matter 31 (but not to contact with the metal electrode 07).

The polarograph circuit 10 connects with an information examination device 40. The information examination device 40 comprises a wave pattern access module 50. The wave pattern access module 50, according to time change, reads an electric voltage-electric current value (a polarogram) and stores the obtained polarogram in a memory device 60.

A comparison module 70 connects with the memory device 60 to read the stored polarogram in the memory device 60, and compares with a digit or graph from a standard determination module 80 to obtain a comparison result 90 and deliver the comparison result 90 to a display device 100. The display device 100 can be a computer monitor, a printing device or wire/wireless network system so that the result can be delivered to a distance terminal.

The standard determination module 80 is an examination standard to be based on to determine the correlative physiological condition of a polarogram, wherein the source is from obtained polarograms via examining physiological conditions of known examinees. The obtaining procedures as follow:

1. Finding a group of examinees of whom the physiological conditions are assured. For example, those are being known that they have been infected by a certain virus or medicined with some designated drugs, etc.
2. According to standard medical clinical experiment methods, collecting the examinees' urine and examining it with a polarograph of the solid state electrode.
3. Storing the obtained polarograms in the data examination device 40 and recording individually the correspondent physiological condition of each polarogram to build a polarogram physiological condition database to become as the standard determination module 80.

One preferred embodiment is: first, the wave pattern access module 50 reads one obtained polarogram every 0.001 second from the polarograph circuit 10 for total 5 seconds, that makes total 5000 electric voltage-current values. The 5000 data is the polarogram's wave pattern data of the urine's examining matter 31. For an easy reference, it is short-named a polarogram $\alpha$.

Figure 4:
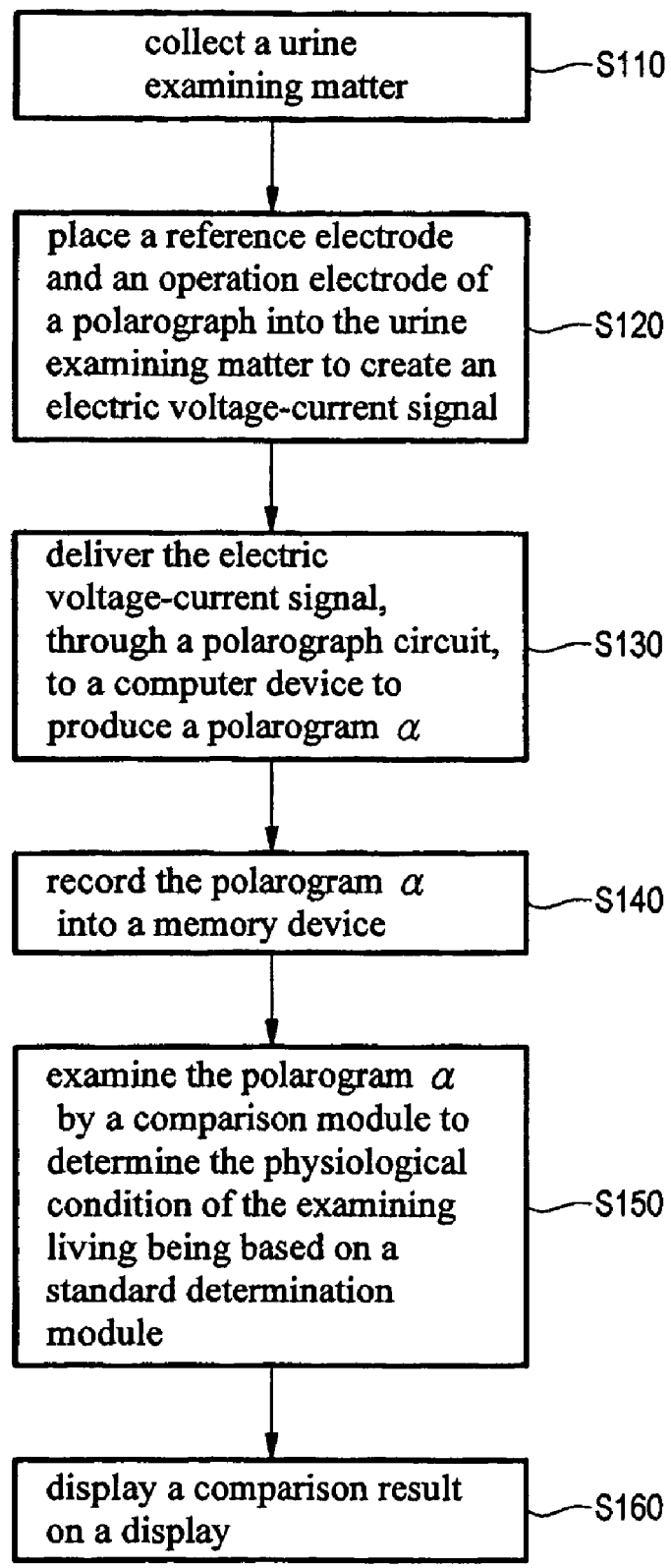
FIG. 4 is a flow chart view of a system applied to automatically examining trace organic matter in urine of this invention.

The standard determination module 80 has records of N data of polarograms of various physiological conditions. The comparison module 70 is functioned for comparison of the polarogram $\alpha$ with wave pattern data in the standard determination module 80. In short, it's functioned like a kind of checking up with indexes. FIG. 4 is a comparison flow view of one embodiment of this invention. First, a urine examining matter 31 is collected (S110), the reference electrode 07 and the operation electrode 08 of a polarograph are placed in the urine examining matter 31, and an electric voltage-current signal is created (S120). The electric voltage-current signals, through a polarograph circuit 10, are delivered to a computer device and produces a polarogram a (S130), and the polarogram $\alpha$ is recorded into a memory device (S140). Based on a standard determination module 80, a comparison module 70 examines the polarogram a to determine the physiological condition of the examining living being (S150). For example, the polarogram $\alpha$ is determined similar with number X wave pattern datum of the standard determination module 80, and the number X wave pattern datum is from an urine examining matter of a living being of some certain unusual physiological condition. Thus, it means the urine examining matter 31 of a provider P (examinee P) also has the same physiological condition of the unusual living being. Finally, the comparison result is displayed on a display device (S160).

The procedures of the comparison method of a comparison module 70 in this embodiment are:

1. Reading the polarogram $\alpha$ in the memory device 60;
2. Subtracting the 5000 data of the polarogram a with the 5000 data of the first polarogram in the standard determination module 80, and separately obtaining an absolute value each. For example, taking the first data of the polarogram a to subtract with the first voltage value of the first polarogram in the standard determination module 80 to obtain the first absolute value, and likewise until all 5000 voltage value data are finished the subtraction and 5000 absolute values are obtained;
3. Totaling the 5000 absolute values and recording it as the first variation value;
4. Repeating steps 2 and 3 until all the polarograms in the standard determination module 80 completed the comparison. For the time being, if the standard determination module 80 has 1000 polarograms, there will be 1000 variation value data individually in correspondence with the 1000 polarograms in the standard determination module 80;
5. Sorting all variation values proportionally with sizes;
6. Taking the smallest 10 values and the correspondent polarogram in the standard determination module 80 together with the correspondent physiological conditions to be delivered to a comparison result 90;
7. Displaying the comparison result 90.

In this embodiment, various modules in the data examination device 40 can be either hardware or software, which to people in the information technology area is an achievable known art.

The comparison method of the comparison module 70 in this embodiment is to use an absolute value totaling method. However, in mathematical operation, the one mentioned above is not the only method to determine a variation difference. For example, a method of squaring individually differences of subtractions and then summing them up is also known to one skilled in the art intended to be included within the scope of this invention.

The data in the standard determination module 80 can also be characteristic marks of polarograms of various physiological conditions, not whole complete polarograms. When the comparison module 70 is processing a comparison, it can aim to the characteristic marks of this portion to process the examination more accurately.

In addition, applying this invention with network information technology can do more of massive and regional living body measurements and data compiling works to understand and examine the unusual physiological conditions of living being society.

This invention being thus described, it will be obvious that the same may be varied in many ways. Such variations are not to be regarded as a departure from the spirit and scope of this invention, and all such modifications as would be obvious to one skilled in the art are intended to be included within the scope of the following claims.

What is claimed is:

1. A method of analyzing and examining trace organic matter in urine utilizing polarography, wherein procedures of the examination comprise:

collecting urine examining matter;

putting the urine examining matter in a reference electrode of a polarograph and dipping an operation electrode of the polarograph into the urine examining matter to cause the operation electrode and the reference electrode to produce a voltage-current signal in between;

delivering the voltage-current signal through a polarograph circuit to a computer device to produce a polarogram $\alpha$;

recording the polarogram $\alpha$ in a memory device;

examining the polarogram $\alpha$ by a comparison module based on a determination standard to determine an examinee's physiological condition; and displaying a result by a display device after comparison, wherein the comparison module, based on the determination standard, examines the polarogram $\alpha$ to determine the physiological condition of the examinee;

reading the polarogram α recorded in a wave pattern access module from the memory device;

comparing the polarogram α with data of a standard determination module to obtain variation values; and taking at least one wave pattern datum of a smallest variation value from the variation values to be a comparison result.

2. A method of analyzing and examining trace organic matter in urine utilizing polarography, wherein procedures of the examination comprise:

collecting urine examining matter;

putting the urine examining matter in a reference electrode of a polarograph and dipping an operation electrode of the polarograph into the urine examining matter to cause the operation electrode and the reference electrode to produce a voltage-current signal in between;

delivering the voltage-current signal through a polarograph circuit to a computer device to produce a polarogram α;

recording the polarogram α in a memory device;

examining the polarogram α by a comparison module based on a determination standard to determine an examinee's physiological condition; and displaying a result by a display device after comparison, wherein the comparison module, based on the determination standard, examines the polarogram α to determine the physiological condition of the examinee;

reading the polarogram α by the comparison module in the memory device and subtracting the polarogram α with plural pieces of polarograms in a standard determination module to obtain variation absolute values; and choosing a smallest variation value from the variation absolute values as a comparison result.

* * * * *